United States Patent
Jöst et al.

(10) Patent No.: US 6,647,600 B1
(45) Date of Patent: Nov. 18, 2003

(54) HOOK AND LOOP FASTENER FOR FLAT MATERIALS

(75) Inventors: Manfred Jöst, Hemsbach (DE); Dieter Groitzsch, Hirschberg (DE); Gerhard Schaut, Hemsbach (DE)

(73) Assignee: Firma Carl Freudenberg, Weinheim (DE)

( * ) Notice: Subject to any disclaimer, the term of this patent is extended or adjusted under 35 U.S.C. 154(b) by 0 days.

(21) Appl. No.: 09/889,991

(22) PCT Filed: Jan. 19, 2000

(86) PCT No.: PCT/EP00/00371

§ 371 (c)(1),
(2), (4) Date: Jul. 25, 2001

(87) PCT Pub. No.: WO00/42964

PCT Pub. Date: Jul. 27, 2000

(30) Foreign Application Priority Data

Jan. 25, 1999 (DE) .......................................... 199 02 762

(51) Int. Cl.⁷ .......................... A44B 18/00; B32B 27/00
(52) U.S. Cl. ............................ 24/442; 24/306; 24/445; 24/451; 24/452; 428/92; 428/99; 428/100; 604/373; 604/391
(58) Field of Search ....................... 24/442, 304, 306, 24/445, 448, 451, 452

(56) References Cited

U.S. PATENT DOCUMENTS

| 4,033,938 A | * | 7/1977 | Augurt et al. | 260/78.3 R |
| 4,041,203 A | * | 8/1977 | Brock et al. | 428/157 |
| 4,894,060 A | * | 1/1990 | Nestegard | 604/391 |
| 4,931,344 A | * | 6/1990 | Ogawa et al. | 428/100 |
| 5,326,612 A | * | 7/1994 | Goulait | 428/100 |
| 5,354,591 A | * | 10/1994 | Ott et al. | 428/99 |
| 5,681,302 A | * | 10/1997 | Melbye et al. | 604/373 |
| 5,735,840 A | * | 4/1998 | Kline et al. | 604/391 |
| 5,888,607 A | * | 3/1999 | Seth et al. | 428/92 |
| 5,907,872 A | * | 6/1999 | Alberts et al. | 2/243.1 |
| 5,928,212 A | * | 7/1999 | Kline et al. | 604/391 |

FOREIGN PATENT DOCUMENTS

| EP | 0 258 015 | 3/1988 |
| EP | 0 765 616 | 4/1997 |
| WO | 95/17111 | 6/1995 |

OTHER PUBLICATIONS

R. Ernst, "*Wörterbuch der industriellen Technik*" [Dictionary of Engineering and Technology], vol. II, English–German, fifth edition, Wiesbaden: Oscar Brandstetter Verlag, 1985, p. 814.

J. Lünenschloss, "*Vliesstoffe*" [Nonwoven Fabrics], Stuttgart–New York: Georg Thieme Verlag, 1982, p. 54. *.

* cited by examiner

*Primary Examiner*—Victor Sakran
(74) *Attorney, Agent, or Firm*—Kenyon & Kenyon

(57) ABSTRACT

A hook and loop fastener for flat structures, particularly for textile products, having a hook part and an interlocking part, the interlocking part being made of a nonwoven composite having worked-in, textured, polymeric threads, the nonwoven composite being used as support for the textured threads, and the textured threads forming the loops for the hooks.

30 Claims, 1 Drawing Sheet

HOOK AND LOOP FASTENER FOR FLAT MATERIALS

FIELD OF THE INVENTION

The present invention relates to a hook and loop fastener for flat materials.

BACKGROUND INFORMATION

So-called hook and loop fasteners, which very simply and quickly permit the fastening of various flat materials, are increasingly used today. Both the fastening of edges adjoining one another, as well as use as fastener straps or the like are customary. The hook and loop fasteners are generally made of two components, and specifically the hook part made of extruded single-hooked, double-hooked or mushroom-shaped elevations, and an interlocking entanglement part having a loop-like arrangement of fibers or threads for the hook part to hook into. Differentiation is generally made between very sturdy hook and loop fasteners, for example, on shoes which must bear a great number of closings and openings, and those hook and loop fasteners which are only closed and opened a few times, e.g., on disposable products. Such disposable products are, for example, hook and loop fasteners on hygiene products such as children's diapers or incontinence products for adults.

International Published Patent Application No. WO 95/17111 describes a hook and loop fastener for baby diapers and incontinence products. The hook part is made of a base layer having hook members. The interlocking part is formed from a backing layer and an entanglement material, the loop entanglement material being disposed below the reinforcement lining, and the loops being poked through by needle-punching the loop material through the reinforcement material. Such a hook and loop fastener is of low stability, particularly when a layer of staple fibers is used as loop material.

European Published Patent Application No. 0 765 616 deals with the interlocking part of a hook and loop fastener, in which use is made of a mechanically or hydrodynamically needle-punched non-woven fabric made of bicomponent thermoplastic fibers. The nonwoven fabric is guided through a roll nip space between two rollers, in which one roller is heated up above the melting point of the thermoplastic fibers, and the other is heated to a point perceptibly below the melting point of the thermoplastic fibers. Due to the temperature gradient formed, the one side of the nonwoven fabric is fused to form a sheeting-like surface, and the other side remains unbonded on the surface. The needling process produces convexities on the fiber surface which have a plurality of loops that make it possible for the hooks to hook in. The stability of the fastener leaves something to be desired in this specific embodiment, as well. It is likewise disadvantageous that here, as in the hook and loop fastener described above, crimped fibers are used and a reasonably justifiable hook and loop fastener can only be achieved when the loop layer is well set in itself and is optionally provided with a support layer.

European Published Patent Application No. 0 258 015 describes various arrangements for producing interlocking parts. The interlocking part is made from a nonwoven, a needlefelt/needle-punched nonwoven or a knit fabric and a thermoplastic resin layer joined thereto by bonding. The stability of such an interlocking part is determined by the bonding process and the thickness of the resin layer. Since the resin layer is very thin, e.g., 0.001 to 0.002 inches, and the bonding process is difficult to perform, the resulting stability may be inadequate.

SUMMARY

An object of the present invention is to provide an interlocking loop part for a hook and loop fastener which is easy to produce and exhibits high stability. The objective is achieved according to the present invention in that the interlocking part is made of a nonwoven fabric composite having worked-in, textured, polymeric threads, the nonwoven composite being used as support for the textured threads, and the textured threads forming the loops for the hooks of the hook part. The interlocking part thus formed exhibits extremely favorable properties, and is clearly superior in effectiveness to conventional hook parts made of non-woven fabrics having crimped fibers as the actual interlocking medium. In the example embodiment of the present invention, the nonwoven fabric, i.e., its fibers, is not the contact point for the interlocking, but rather the non-woven fabric is used simply as support for the textured threads which are worked in by raschel knitting and which form the interlocking loops.

DETAILED DESCRIPTION

Figure 1:
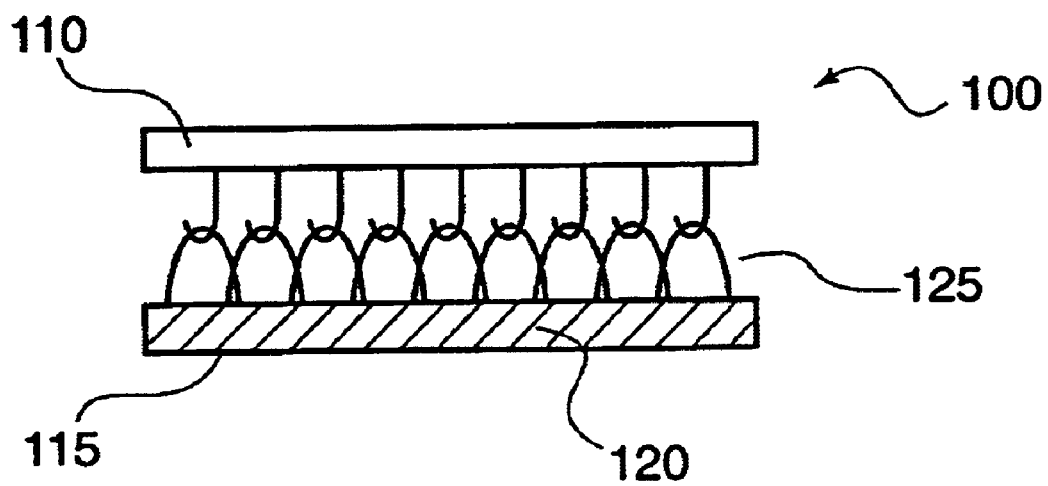
FIG. 1 illustrates a first exemplary hook and loop fastener according to the present invention.
Figure 2:
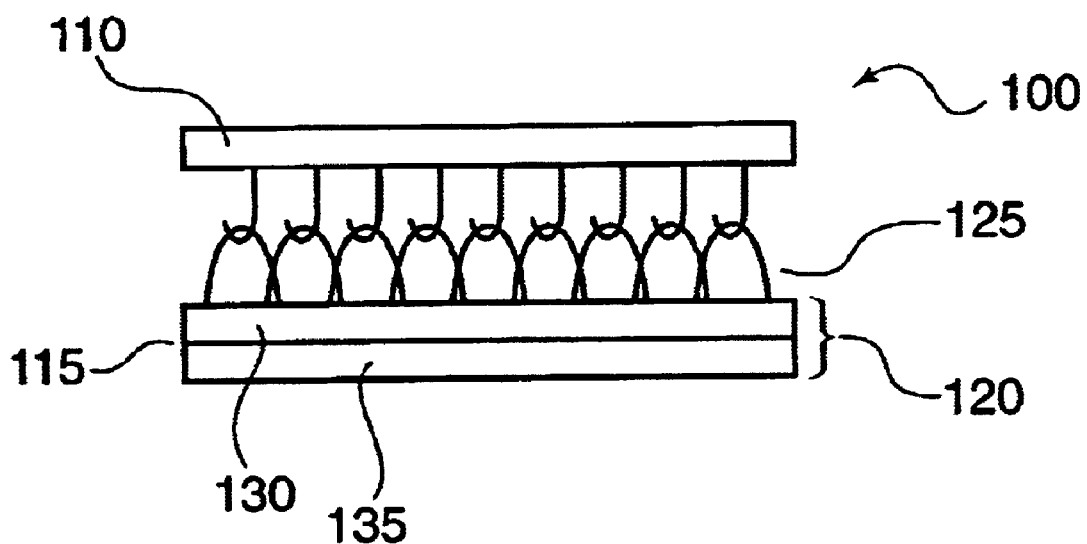
FIG. 2 illustrates a second exemplary hook and loop fastener according to the present invention.

Referring now to FIG. 1, there is seen an exemplary hook and loop fastener 100 according to the present invention, which may, for example, be used for flat materials and textile products. Hook and loop fastener 100 includes a hook part 110 and an interlocking part 115 made of a nonwoven fabric 120 forming a support for textured polymeric threads 125, which define loops of the interlocking part 115. Although FIG. 1 shows the nonwoven fabric 120 including a single layer, it should be appreciated that the nonwoven fabric 120 may include a plurality of layers, for example, two layers 130, 135, as shown in FIG. 2.

To implement the present invention, it is also possible to form the nonwoven composite from non-crimped fibers of high stability. In so doing, continuous fibers may be used.

It is also possible to use microfibers if the intention is to achieve a particular softness of the nonwoven composite.

One example embodiment is particularly favorable in which the nonwoven composite is formed from at least two nonwoven-fabric layers. Here, different variations are possible.

A good design approach is achieved if the nonwoven composite is made of a spunbonded nonwoven/meltblown composition or a spunbonded nonwoven/meltblown/spunbonded nonwoven composition. Here, a very loose flimsy intermediate layer is achieved between two spunbonded nonwovens made of continuous threads.

The individual layers can be loosely placed one upon the other. However, before introducing the threads, it is also possible to weld the nonwoven composite, the welding being distributed like a pattern. Here, it is possible to use spot-welding technology or even ultrasonic welding. Another possibility is to calender the nonwoven composite over the entire surface before introducing the threads. In special cases, bonding the threads using nonwoven fabrics containing binding agents is also conceivable.

In addition to spunbonded nonwovens, generally staple-fiber nonwovens or wet-laid nonwovens can also be used. However, spunbonded nonwovens may be preferred for reasons of stability as well as cost.

If the nonwoven composite is made completely or partially of microfibers, they can be attained by conventional splitting methods through high-pressure treatment, water-jet treatment, hot-water or steaming treatment, or by dry mechanical treatment.

It is also possible to bond the nonwoven composite by high-pressure water jet. In so doing, however, care should be taken that the nonwoven composite is not macro-perforated.

In a number of application cases, it may desired that the closure region of the hook and loop fastener be applied in color, in particular when the hook and loop fastener is stuck onto the article of purely practical value, and the intention is to obtain an adhesive surface. Such a surface can be attained by smoothing off polishing. This can be implemented particularly simply when working with a meltblown layer which can be smoothed off in a sheet-like manner by guiding it, for example, over a heated roller.

In order to achieve a good printing and adhesive surface, respectively, the nonwoven composite can also be provided with a lower layer made of a sheeting upon which the printing, i.e., the adhesive layer is applied. The sheeting can be bonded by extrusion with the upper layer made of nonwoven fabric.

Generally a mass per unit area of 7 to 70 g/qm, e.g., 10 to 50 g/qm, is selected for the nonwoven composite. The textured threads themselves can be made of the same or different homo-thread and/or bicomponent filaments. However, threads made of biologically degradable polymers may be used in order to achieve the degradability desired for diapers.

The textured threads have a titer of 20 to 200 dtex, e.g., from 30 to 120 dtex, and are introduced as warp threads into the nonwoven composite. In so doing, a zig-zag pattern distribution can be made in the direction of the warp. After the threads are sewn in and the thread-reinforced nonwoven composite is relaxed, the length of the fabric can shorten by 0 to 10%.

The number of warp threads is 3 to 25 per inch, e.g., 20 per inch. A sufficient number of loops is thereby formed for the interlocking. The number of stitches loops is 2 to 4 per centimeter.

The interlocking part of the present invention for a hook and loop fastener may be used for hygiene products that are used once such as children's diapers or incontinence products for adults. Uses on other disposable products for which the hook and loop fastener is required to be closed and reopened no more than 10 times are also conceivable. This is the case, for instance, for non-reusable operating-room gowns or occupational safety and health clothing.

Generally, when implementing the present invention, a nonwoven composite is used made of a plurality of layers, at least one layer being composed of microfibers. The microfiber layer is covered at least on one side with a standard spunbonded nonwoven or staple-fiber nonwoven fabric. On at least one of the outer layers of the nonwoven composite, an adhesion-friendly layer is selected which is provided with a multi-color printing prior to working in the textured threads by raschel knitting. In addition, an adhesive, preferably a contact adhesive, can be applied on the side which is not imprinted.

However, in many cases it is favorable if the nonwoven composite is provided with a sheeting film which can be monolithic or contain micropores. Depending on its polymer structure, the monolithic sheeting can be water-vapor permeable, or else can also represent a barrier against water vapor. For example, polyolefin sheetings are used which optionally contain adhesion or tackiness promoters, or, by high-energy radiation, e.g., in the presence of radical monomers, have been constructed to be more adhesion-friendly for the bonding process.

The manufacturing form of the nonwoven composite provides for feeding the nonwoven composite in stretched form to a raschel-knitting process for introducing the warp threads. When working with a linear alignment of the threads worked in by raschel knitting, the elongation may be effected only in this direction. In the case of a zigzag guidance of the textured threads, an elongation of the elastic nonwoven is possible in the longitudinal direction and the transverse direction, or only in one of the two directions. Due to the subsequent relaxation of the nonwoven composite, the number of stitches per unit of length and the height of the loops increase corresponding to the shortening of length.

What is claimed is:

1. A hook and loop fastener for flat materials and textile products, comprising a hook part and an interlocking part, the interlocking part made of a nonwoven being provided with polymeric threads which define loops of the interlocking part, wherein the threads are textured and are worked into a support made of a nonwoven composite.

2. The hook and loop fastener according to claim 1, wherein, prior to introducing the threads, the nonwoven composite is welded, the welding being distributed like a pattern.

3. The hook and loop fastener according to claim 1, wherein the nonwoven composite is calendered over the entire surface prior to introducing the threads.

4. The hook and loop fastener according to claim 1, wherein the nonwoven composite is formed from at least one upper layer made of nonwoven fabric and one lower layer made of a sheeting.

5. The hook and loop fastener according to claim 1, wherein the nonwoven composite has a mass per unit area of 7 to 70 g/qm.

6. The hook and loop fastener according to claim 5, wherein the nonwoven composite has a mass per unit area of 10 to 50 g/qm.

7. The hook and loop fastener according to claim 1, wherein the textured threads have a titer (thread weight) of 20 to 200 dtex.

8. The hook and loop fastener according to claim 7, wherein the textured threads have a titer (thread weight) of 30 to 120 dtex.

9. The hook and loop fastener according to claim 1, wherein the textured threads are introduced as warp threads into the nonwoven composite.

10. The hook and loop fastener according to claim 1, wherein the number of warp threads (warp density) is 3 to 25 per 2.54 cm.

11. The hook and loop fastener according to claim 10, wherein the number of warp threads (warp density) is 20 per 2.54 cm.

12. The hook and loop fastener according to claim 1, wherein the number of stitches is 2 to 4 per cm.

13. A hook and loop fastener for flat materials and textile products, comprising a hook part and an interlocking part, the interlocking part made of a nonwoven being provided with polymeric threads which define loops of the interlocking part, wherein the threads are textured and are worked into a support made of a nonwoven composite;

wherein the nonwoven composite is made of non-crimped fibers of high stability.

14. The hook and loop fastener according to claim 13, wherein the fibers are continuous fibers.

15. The hook and loop fastener according to claim 13, wherein the fibers are microfibers.

16. A hook and loop fastener for flat materials and textile products, comprising a hook part and an interlocking part, the interlocking part made of a nonwoven being provided with polymeric threads which define loops of the interlocking part, wherein the threads are textured and are worked into a support made of a nonwoven composite;

wherein the nonwoven composite is formed from at least two nonwoven layers.

17. A hook and loop fastener for flat materials and textile products, comprising a hook part and an interlocking part, the interlocking part made a nonwoven being provided with polymeric threads which define loops of the interlocking part, wherein the threads are textured and are worked into a support made of a nonwoven composite;

wherein the nonwoven composite is made of one of a spunbonded nonwoven/meltblown composition and a spunbonded nonwoven/meltblown/spunbonded nonwoven composition.

18. The hook and loop fastener according to claim 17, wherein the meltblown layer is smoothed off in a sheeting-like manner prior to introducing the threads.

19. A hook and loop fastener for flat materials and textile products, comprising a hook part and an interlocking part, the interlocking part made of a nonwoven being provided with polymeric threads which define loops of the interlocking part, wherein the threads are textured and are worked into a support made of a nonwoven composite;

wherein the nonwoven composite is formed from at least one upper layer made of nonwoven fabric and one lower layer made of a sheeting; and wherein the sheeting is bonded by extrusion to the upper layer made of nonwoven fabric.

20. A hook and loop fastener for flat materials and textile products, comprising a hook part and an interlocking part, the interlocking part made of a nonwoven being provided with polymeric threads which define loops of the interlocking part, wherein the threads are textured and are worked into a support made of a nonwoven composite;

wherein at least one of the nonwoven fabrics and the textured threads are made of at least one of homo-thread and bicomponent filaments.

21. A hook and loop fastener for flat materials and textile products, comprising a hook part and an interlocking part, the interlocking part made of a nonwoven being provided with polymeric threads which define loops of the interlocking part, wherein the threads are textured and are worked into a support made of a nonwoven composite;

wherein the nonwoven composite and the textured threads are made of biologically degradable polymer.

22. A method for producing a hook and loop fastener for flat materials and textile products, the fastener including a hook part and an interlocking part, the interlocking part being made of a nonwoven fabric provided with polymeric threads defining loops of the interlocking part, the threads being textured and worked into a support made of a nonwoven composite, the method comprising: feeding the nonwoven composite in stretched form to a raschel-knitting process for introducing the warp threads.

23. A hook and loop fastener, comprising:

a hook part; and an interlocking part including a nonwoven fabric support and a plurality of textured polymeric threads worked into the nonwoven fabric support;

wherein the textured polymeric threads define loops.

24. The hook and loop fastener according to claim 23, wherein the nonwoven fabric support includes at least two nonwoven fabric layers.

25. The hook and loop fastener according to claim 23, wherein the nonwoven fabric support has a mass per unit area of 7 to 70 g/qm.

26. The hook and loop fastener according to claim 25, wherein the nonwoven fabric support has a mass per unit area of 10 to 50 g/qm.

27. A hook and loop fastener, comprising:

a hook part; and an interlocking part including a nonwoven fabric support and a plurality of textured polymeric threads worked into the nonwoven fabric support;

wherein the textured polymeric threads define loops; and wherein the nonwoven fabric support includes one of non-crimped continuous fibers and non-crimped microfibers.

28. A hook and loop fastener, comprising:

a hook part; and an interlocking part including a nonwoven fabric support and a plurality of textured polymeric threads worked into the nonwoven fabric support;

wherein the textured polymeric threads define loops; and wherein the nonwoven fabric support includes one of a spunbonded nonwoven/meltblown fabric composition and a spunbonded nonwoven/meltblown/spunbonded nonwoven fabric composition.

29. A hook and loop fastener, comprising:

hook part; and an interlocking part including a nonwoven fabric support and a plurality of textured polymeric threads worked into the nonwoven fabric support;

wherein the textured polymeric threads define loops; and wherein at least one of the nonwoven fabric support and the textured polymeric threads includes at least one of homo-thread and bicomponent filaments.

30. A hook and loop fastener for flat materials and textile products, comprising a hook part and an interlocking part, the interlocking part made of a nonwoven being provided with polymeric threads which define loops of the interlocking part, wherein the threads are textured and are worked into a support made of a nonwoven composite;

wherein the nonwoven fabric support and the textured polymeric threads include a biologically degradable polymer.

* * * * *